United States Patent
Rezach

(10) Patent No.: US 7,585,299 B2
(45) Date of Patent: Sep. 8, 2009

(54) DORSAL ADJUSTING SPINAL CONNECTOR ASSEMBLY

(75) Inventor: Alan Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 408 days.

(21) Appl. No.: 11/356,939

(22) Filed: Feb. 17, 2006

(65) Prior Publication Data

US 2007/0233066 A1    Oct. 4, 2007

(51) Int. Cl.
  A61B 17/56 (2006.01)
  A61B 17/70 (2006.01)
  A61B 17/80 (2006.01)
  A61B 17/88 (2006.01)

(52) U.S. Cl. .................. 606/60; 606/246; 606/250; 606/257; 606/264; 606/277; 606/278; 606/279; 606/286

(58) Field of Classification Search .................. 606/60, 606/61, 72, 73, 66, 252, 278, 264, 266, 279, 606/301, 59, 86 A, 250
See application file for complete search history.

(56) References Cited

U.S. PATENT DOCUMENTS

| | | | |
|---|---|---|---|
| 4,569,338 A | 2/1986 | Edwards | |
| 4,827,918 A | 5/1989 | Olerud | |
| 5,047,029 A | 9/1991 | Aebi et al. | |
| 5,053,034 A | 10/1991 | Olerud | |
| 5,254,118 A | 10/1993 | Mirkovic | |
| 5,527,314 A | 6/1996 | Brumfield et al. | |
| 5,534,002 A | 7/1996 | Brumfield et al. | |
| 5,562,662 A | 10/1996 | Brumfield et al. | |
| 5,575,791 A | 11/1996 | Lin | |
| 5,643,263 A | 7/1997 | Simonson | |
| 5,709,685 A * | 1/1998 | Dombrowski et al. | 606/278 |
| 5,810,817 A * | 9/1998 | Roussouly et al. | 606/250 |
| 5,885,285 A | 3/1999 | Simonson | |
| 5,938,663 A | 8/1999 | Petreto | |
| 5,947,965 A | 9/1999 | Bryan | |
| 5,947,967 A * | 9/1999 | Barker | 606/278 |
| 6,179,838 B1 | 1/2001 | Fiz | |
| 6,183,473 B1 | 2/2001 | Ashman | |
| 6,210,413 B1 | 4/2001 | Justis et al. | |
| 6,248,107 B1 | 6/2001 | Foley et al. | |
| 6,520,962 B1 | 2/2003 | Taylor et al. | |
| 6,562,038 B1 | 5/2003 | Morrison | |
| 6,565,569 B1 | 5/2003 | Assaker et al. | |
| 6,569,164 B1 | 5/2003 | Assaker et al. | |
| 6,685,705 B1 | 2/2004 | Taylor | |

(Continued)

FOREIGN PATENT DOCUMENTS

DE    195 12 709 A1    10/1996

(Continued)

*Primary Examiner*—Thomas C. Barrett
*Assistant Examiner*—Sameh Boles

(57) ABSTRACT

A connector assembly includes a coupling body for securing an elongate member to an implant engaged to the spinal column. The elongate member is offset to one side of and transversely oriented to the implant. The coupling body includes a first passage for receiving the implant and a second passage for receiving the elongate member and a clamping member positioned about the elongate member. The coupling assembly also includes an engaging member that engages the coupling body and contacts the clamping member to clampingly engage the elongate member with the clamping member while manipulating the coupling body positioned about the implant to engage the coupling body to the implant.

20 Claims, 4 Drawing Sheets

U.S. PATENT DOCUMENTS

| | | |
|---|---|---|
| 6,749,612 B1 | 6/2004 | Conchy et al. |
| 6,881,215 B2 | 4/2005 | Assaker et al. |
| 2002/0042613 A1* | 4/2002 | Mata .......................... 606/59 |
| 2004/0138661 A1 | 7/2004 | Bailey |
| 2004/0254574 A1* | 12/2004 | Morrison et al. .............. 606/61 |
| 2005/0113835 A1 | 5/2005 | Ashman |
| 2006/0058787 A1* | 3/2006 | David .......................... 606/61 |

FOREIGN PATENT DOCUMENTS

WO     WO 00/15125 A     3/2000

* cited by examiner

DORSAL ADJUSTING SPINAL CONNECTOR ASSEMBLY

BACKGROUND

Spinal implants can be engaged to or along one or more vertebrae of the spinal column for the treatment of various spinal conditions. Fasteners can be provided to secure the implant to a particular location along the spinal column. The implants can be provided to stabilize the spinal column for treatment, either by fixing the spinal column or by permitting at least some motion of the stabilized motion segments.

Multi-axial and uni-axial screws have been employed for securing elongated implants, such as rods or plates, along one or more motion segments of the spinal column. Such fasteners can comprise many components or parts that make placement and manipulation of the fastener and the elongated implant cumbersome during surgery to achieve the desired position relative to the spinal anatomy. Fasteners that facilitate securement of the elongated implant in a desired positioning along the spinal column can enhance spinal stabilization procedures.

SUMMARY

According to one aspect, a connector assembly includes a coupling body for securing an elongate member to an implant engaged to the spinal column. The elongate member is offset to one side of and transversely oriented to the implant. The coupling body includes a first passage for receiving the implant, a second passage for receiving the elongate member, and a clamping member positioned about the elongate member. The coupling assembly also includes an engaging member that engages the coupling body and contacts the clamping member to clampingly engage the elongate member with the clamping member while forcing the coupling body positioned about the implant into engagement with the implant.

According to one aspect, a system for stabilizing a bony segment includes an elongate member positionable along the bony segment, an implant including a proximal portion and a distal portion engageable to the bony segment with the proximal portion in a transverse orientation to the elongate member, and a connector assembly for connecting the elongate member to the implant. The connector assembly includes a coupling body, an engaging member and a clamping member. The coupling body has a pair of arms extending alongside one another between a free end and an opposite end. A connecting portion extends between the pair of arms at the opposite ends and defines a first passage receiving the proximal portion of the implant therethrough. The pair of arms defines a second passage receiving the elongate member therethrough in the transverse orientation. The clamping member can be positioned about the elongate member in the second passage, and the engaging member can be engaged to the first arm in a first position. The engaging member is movable toward the clamping member from the first position to contact the clamping member to clampingly engage the clamping member to the elongate member while flexing the coupling body about the connecting portion to engage the coupling body to the proximal portion of the implant.

According to another aspect, a system for stabilizing a bony segment includes an elongate member positionable along the bony segment, an implant including a proximal portion and a distal portion engageable to the bony segment with the proximal portion in a transverse orientation to the elongate member, and a connector assembly for connecting the elongate member to the implant. The connector assembly includes a coupling body, an engaging member and a clamping member. The coupling body has a connecting portion extending between a pair of arms. The arms extend from the connecting portion alongside one another and form a gap therebetween. The connecting portion defines a first passage receiving the proximal portion of the implant therethrough and the pair of arms defines a second passage receiving the elongate member therethrough in the transverse orientation. The clamping member is positioned about the elongate member in the second passage, and an engaging member is engaged to the first arm in a first position. The coupling body is configured to move the first arm along the engaging member and away from the clamping member as the engaging member is moved from the first position to contact the clamping member and clampingly engage the clamping member to the elongate member. Movement of the first arm bends the coupling body about the connecting portion and frictionally engages the coupling body to the proximal portion of the implant in the first passage.

According to another aspect, a method for coupling an elongate member to an implant engageable to a spinal column comprises: engaging the implant to a vertebra of the spinal column; positioning an elongate member along the spinal column in a transverse orientation to the implant; positioning a clamping member about the elongate member; positioning a proximal portion of the implant in a first passage of a coupling body; positioning the clamping member in a second passage of the coupling body; engaging an engaging member to the coupling body; contacting the engaging member to the clamping member to clamp the clamping member about the elongate member while simultaneously bending the coupling body with the engaging member to clampingly engage the coupling body to the proximal portion of the implant in the first passage.

These and other aspects will be discussed further below.

DETAILED DESCRIPTION OF THE ILLUSTRATED EMBODIMENTS

Figure 1:
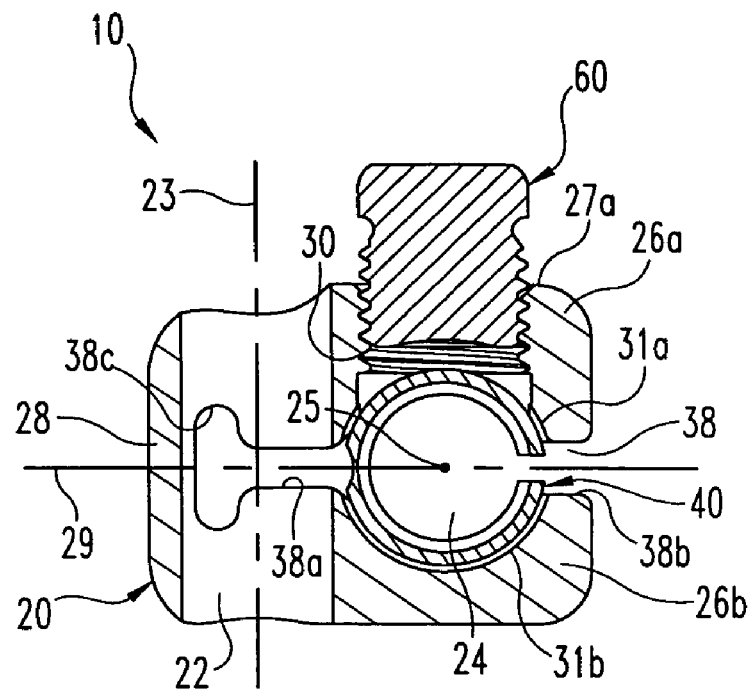
FIG. 1 is a sectional view of a connector assembly.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Figure 9:
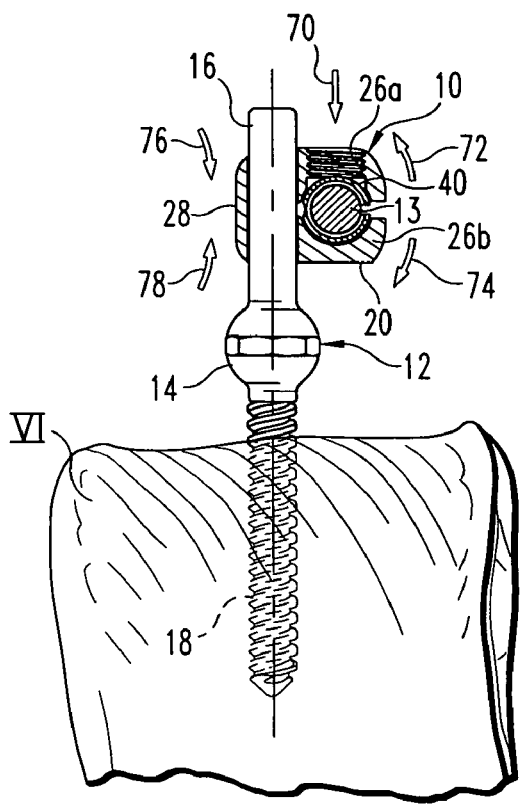
FIG. 9 is an elevation view of an implant engaged to a vertebral body (shown diagrammatically) and a connector assembly (with engaging member removed) positioned about the implant with an elongate member shown in section extending through the connector assembly transversely to and laterally offset from the implant.
Figure 10:
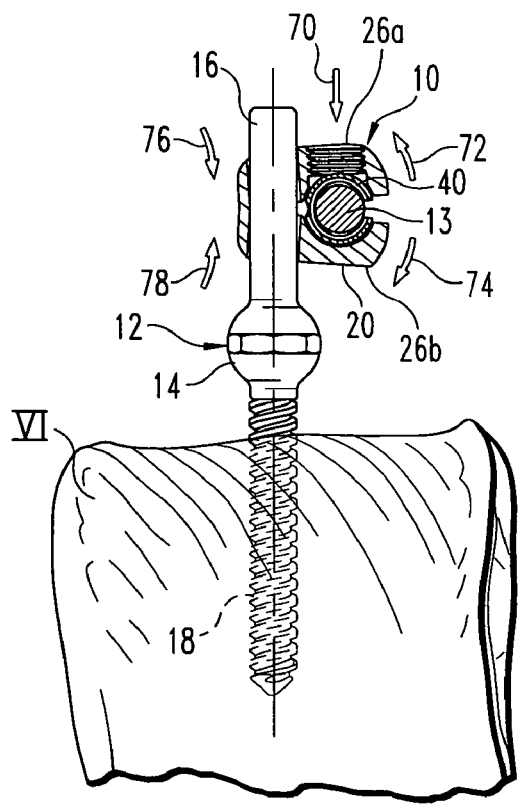
FIG. 10 is the connector assembly, implant and elongate member of FIG. 9 when the clamping member is clampingly engaged to the elongate member and the coupling body is flexed to clampingly engage the implant.

FIG. 1 shows an embodiment of a connector assembly 10, and in FIGS. 9-10 an implant 12 and elongate member 13 are shown coupled to connector assembly 10. Connector assembly 10 is operable to connect implant 12, such as a bone anchor, with elongate member 13, such as a spinal rod, to form an implant system. Implant 12 can be a bone screw or other suitable anchoring device engageable to bone or another implant. The implant can include a portion for engagement with connector assembly 10. Elongate member 13 can be a spinal rod or other member positionable along the spinal column to maintain or assist in maintaining one or more vertebrae in a desired position.

Connector assembly 10 can include a coupling body 20 extending between implant 12 and elongate member 13. Connector assembly 10 can further include a clamping member 40 positioned about elongate member 13 in coupling body 20. Connector assembly 10 can also include an engaging member 60 engageable to coupling body 20. Engaging member 60 is operable to contact clamping member 40 to clampingly engage it about elongate member 13 while simultaneously flexing, deforming or otherwise manipulating coupling body 20 to engage implant 12.

Coupling body 20 can be engaged to a proximal portion 16 of implant 12. In one embodiment, proximal portion 16 can be a post, arm, or other suitable extension or portion for positioning through coupling body 20. Coupling body 20 can include a first passage 22 extending along a first axis 23 and a second passage 24 extending along a second axis 25. First and second axes 23, 25 can extend transversely to one another. In one embodiment, axes 23, 25 are orthogonally oriented relative to one another. Proximal portion 16 of implant 12 can extend through first passage 22 in general alignment with axis 23, and elongate member 13 can extend through second passage 24 in general alignment with axis 25. Accordingly, implant 12 and elongate member 13 can be transversely oriented relative to one another with elongate member 13 laterally or medially offset to one side of implant 12.

Implant 12 in the illustrated embodiment is a bone screw and can include a distal shaft 18 having a thread profile therealong for engaging bone, and an enlarged head 14 between distal shaft 18 and proximal portion 16. Head 14 can include flats or other tool engaging features therearound to engage a driving tool to facilitate engagement of implant 12 to the underlying bone. Various forms for implant 12 are contemplated, including threaded and non-threaded anchors, uniplanar and multi-axial pivoting arrangements. Bone engaging portions in the form of hooks, clamps, spikes, cables, interbody implants, fusion devices, non-cannulated screws, fenestrated screws, and bolts, are also contemplated, for example. In another form, the implant can be connected to another implant, and/or can be a bone plate, staple, and/or cross-connector extending between spinal rods, for example.

Elongate member 13 can be structured either alone or in combination with one or more other elongate members, implants and/or connector assemblies to provide a desired stabilization effect. In the illustrated embodiment, elongate member 13 is a spinal rod structured to extend between at least two connector assemblies 10 secured to the spinal column with corresponding bone engaging implants. Elongate member 13 can also extend between at least one connector assembly 10 and another implant having any type of suitable connection mechanism to secure elongate member 13 to the implant. Various forms for elongate member 13 are contemplated, including rods, tethers, cables, wires, and plates, for example.

Figure 2:
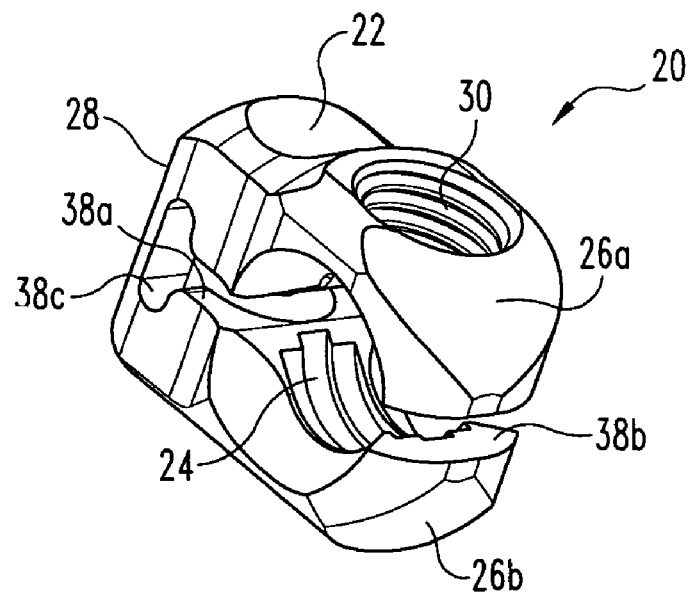
FIG. 2 is a perspective view of a coupling body of the connecting assembly of FIG. 1.
Figure 3:
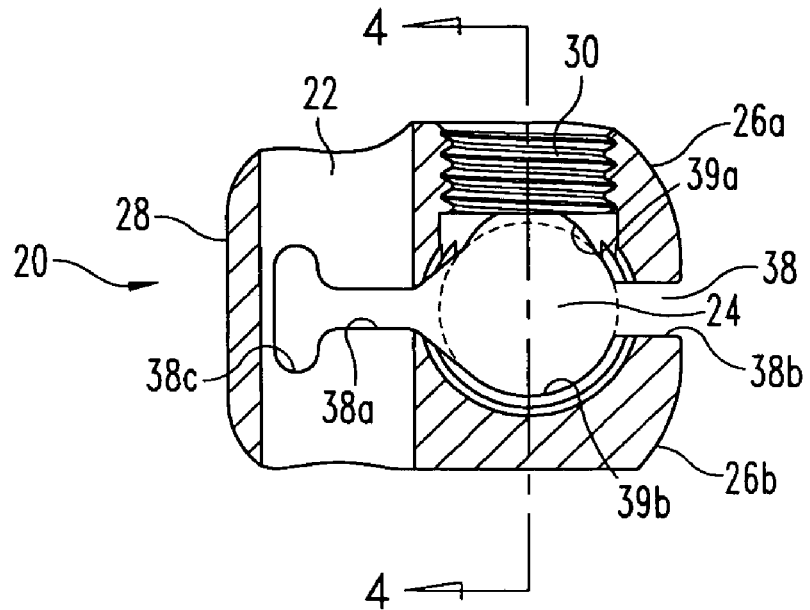
FIG. 3 is a section view of the coupling body of FIG. 2 looking in the same direction as FIG. 1 but with the clamping member and engaging member removed.
Figure 4:
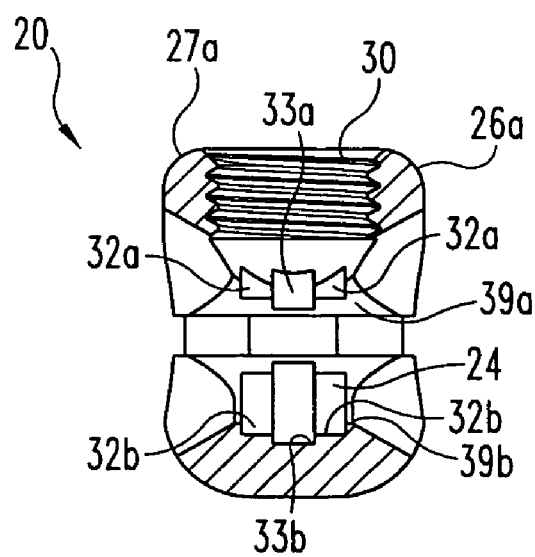
FIG. 4 is a section view along line 4-4 of FIG. 3.

Coupling body 20 is shown in isolation in FIGS. 2-4. Coupling body 20 includes a pairs of arms 26, selectively referred to as a first arm 26a and a second arm 26b. Arms 26a, 26b extend from adjacent free ends to opposite ends that are interconnected by a connecting portion 28 extending therebetween. Connecting portion 28 includes a shape that defines first passage 22 therethrough in a direction that extends transversely to arms 26a, 26b. Furthermore, first and second arms 26a, 26b define respective portions of second passage 24 therebetween.

Coupling body 20 includes a gap 38 extending along an axis 29 that is located between arms 26a, 26b. Gap axis 29 is transversely oriented to longitudinal axis 25 and to longitudinal axis 23. Gap 38 includes an intermediate portion 38a that extends between first and second passages 22 and 24, and an outer portion 38b that extends from second passage 24 to the outer, free ends of arms 26a, 26b. Gap 38 further includes an inner portion 38c in connecting portion 28 that forms a transverse axial extension of gap 38 in the direction of axis 23. The inner portion 38c provides a slotted arrangement that forms reliefs to facilitate flexing, bending, and deforming of coupling body 20 about connecting portion 28, as discussed further below.

First and second arms 26a, 26b include a respective one of the concavely curved inner surface portion 39a, 39b defining second passage 24. As shown in FIG. 4, arms 26a, 26b each include a respective groove 31a, 31b extending about a respective one of the inner surfaces 39a, 39b thereof that define passage 24. Each groove 31a, 31b includes a respective one of the outer portions 32a, 32b and middle portions 33a, 33b extending into the respective inner surface 39a, 39b of first and second arm 26a, 26b. Middle portions 33a, 33b are each deeper than the respective adjacent outer portions 32a, 32b so that an edge is formed between each of the portions of grooves 31a, 31b and the respective adjacent portion of inner surfaces 39a, 39b. These edges can bite into the outer surface of clamping member 40 when clamping member 40 is pressed against one of the arms 26a, 26b, thereby locking clamping member 40 in position in passage 24.

First arm 26a also includes a receptacle 30 extending therethrough in communication with second passage 24. Receptacle 30 opens at a proximal facing surface or side 27a of arm 26a. Receptacle 30 can include an internal thread profile extending therealong to threadingly engage engaging member 60, as discussed further below. The thread profile allows advancement of engaging member 60 in a direction that is transverse to axes 25, 29 and in the same general direction as axis 23. Orientations of receptacle 30 that are oblique relative to axes 25, 29 are also contemplated.

Coupling body 20 can flex about connecting portion 28 in response to movement of at least one of the arms 26a, 26b away from the other and widening of outer portion 38b of gap 38. As arms 26a, 26b rotate or pivot about connecting portion 28, connecting portion 28 can deform or flex toward first passage 22 and into contact with proximal portion 16 of implant 12 to clampingly or frictionally engage implant 12 to coupling body 20.

Figure 5:
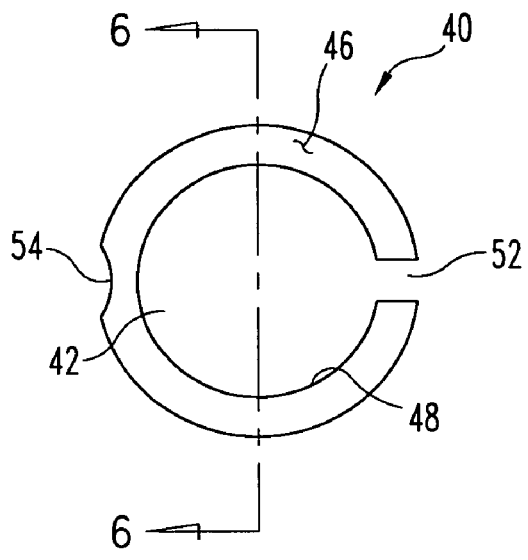
FIG. 5 is an elevation view of a clamping member.
Figure 6:
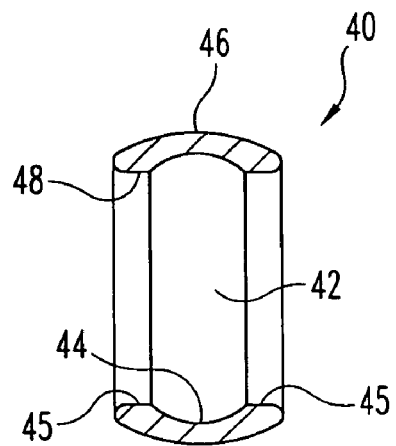
FIG. 6 is a section view through line 6-6 of FIG. 5.

Connector assembly 10 includes clamping member 40 positionable about elongate member 13. Clamping member 40 is shown in isolation in FIGS. 5 and 6, and in second passage 24 in FIG. 1. When clamping member 40 is not engaged with engaging member 60, clamping member 40 can pivot in passage 24 to facilitate orienting coupling body 20, implant 12 and elongate member 13 relative to one another.

Clamping member 40 includes a passage 42 extending therethrough to receive elongate member 13. Clamping member 40 can include an outer surface 46 that defines a spherical shape, and an internal wall 48 defining passage 42. Internal wall 48 includes a central concave portion 44 that is concavely curved and linear end portions 45 extending from central concave portion 44. Clamping member 40 further includes a gap 52 extending axially therealong that allows portions of the clamping member 40 to be moved toward one another by reducing gap 52. Such movement can be facilitated by a hinge 54 formed in clamping member 40 opposite gap 52. In the illustrated embodiment, hinge 54 is formed by reducing a wall thickness of clamping member 40, providing a living or integral hinge.

Other embodiments contemplate other structures for clamping about elongate member 13, including shape memory material and material sufficiently deformable without a hinge. The concavely curved inner wall portion 44 is spaced from elongate member 13, allowing circumferential contact by liner end portions 45 of internal wall 48 with the elongate member 13. This arrangement can reduce binding or twisting that could be created as clamping member 40 is clamped about elongate member 13. Other embodiments contemplate that clamping member 40 contacts elongate member 13 along the entire or substantially all of the length of passage 42, or that clamping member 40 contacts elongate member 13 about a mid-portion of passage 42.

Figure 7:
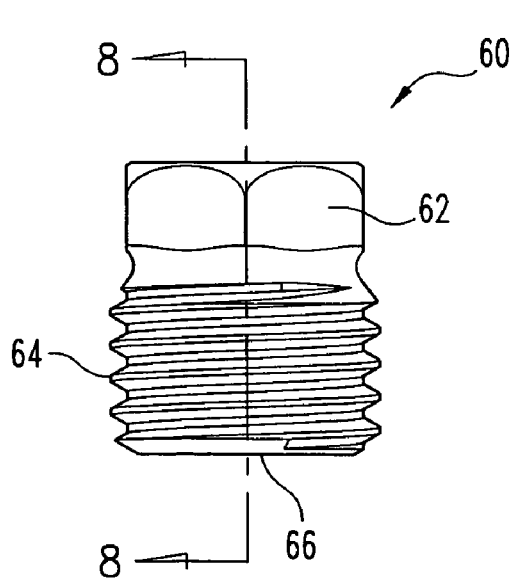
FIG. 7 is an elevation view of an engaging member.
Figure 8:
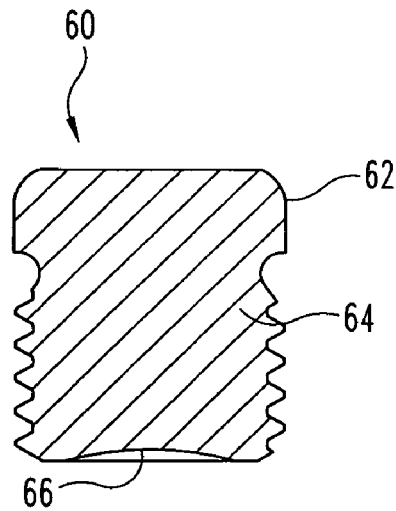
FIG. 8 is a section view through line 8-8 of FIG. 7.

Connector assembly 10 further includes engaging member 60 engageable in receptacle 30 and positionable in contact with clamping member 40 in second passage 24 as shown in FIG. 1. Engaging member 60 is shown in isolation in FIGS. 7-8, and includes a proximal head portion 62, a distal engaging portion 64, and a distal end surface 66. Head portion 62 can be configured to engage a driving tool that can be positioned about head portion 62 or in an internal recess in head portion 62 (not shown). In the illustrated embodiment, head portion 62 includes a non-circular external shape, such as a hex-shape, to receive a driving tool thereabout.

Distal engaging portion 64 of engaging member 60 can include an externally threaded cylindrical body that threadingly engages internal threads along receptacle 30. Engaging member 60 also includes distal end surface 66 that is positionable into contact with clamping member 40 as engaging member 60 is threaded into receptacle 30. Distal end surface 66 can be concavely curved to engage clamping member 40 in form fitting engagement and facilitate rotation of engaging member 60 against clamping member 40. The use of an instrument to drive engaging member 60 against clamping member 40 can provide a mechanical advantage in deforming coupling body 20 by separating arms 26a, 26b about connecting portion 28 and also in deforming clamping member 40 about hinge 54 to close gap 52 and clampingly engage elongate member 13.

Engaging member 60 can include a proximal break-off portion (not shown) that severs upon application of a threshold torque, although embodiments without a break-off portion are contemplated as shown. Engaging member 60 is shown with external threads that engage the internal thread profile along receptacle 30. Other configurations are also contemplated for engagement of engaging member 60 to coupling body 20, including multiple component members with internally and/or externally threaded portions, frictionally engaged members, shape memory members, snap fits, clamps and bayonet-type fits, for example.

As shown in FIGS. 9 and 10, connector assembly 10 can be used in surgical procedures relating to the spine. The surgeon can gain access to a surgical site using any suitable technique, such as through an incision and retraction of tissue, or through minimally invasive access portals or pathways. One or more of the implants 12 can be provided in the form of bone screws that are threadingly implanted into one or more vertebrae V1, such as in the pedicle in a posterior stabilization procedure. Proximal portion 16 can extend dorsally from the pedicle.

Coupling body 20 can be positioned about clamping member 40 with clamping member 40 loosely retained in passage 24. Elongate member 13 can be positioned through clamping member 40. It is contemplated that assembly of coupling body 20 with clamping member 40 and elongate member 13 can be completed prior to implantation of elongate member 13 or during implantation. In either case, elongate member 13 can be positioned along the spinal column with coupling body 20 secured thereto and arms 26a, 26b extending from elongate member 13 toward proximal portion 16 of implant 12. Coupling body 20 can then be positioned over implant 12 with proximal portion 16 extending into first passage 22. First passage 22 can be configured to provide a close, sliding fit with proximal portion 16. Prior to finally securing coupling body 20, the orientation of elongate member 13 relative to coupling body 20 can be adjusted by pivoting coupling body 20 about clamping member 40 in second passage 24.

Engaging member 60 is positioned in receptacle 30 and threaded distally therealong in the direction of arrow 70 to contact clamping member 40. Further advancement of engaging member 60 into receptacle 30 closes gap 52 of clamping member 40 to clampingly engage clamping member 40 about elongate member 13. In addition, clamping arm 26a moves proximally along the threaded portion of engaging member 60 as indicated by arrow 72, and clamping arm 26b moves or deforms in the opposite direction as indicated by arrow 74. Coupling body 24 also bends or flexes about connecting portion 28, as indicated by arrows 76, 78, to deform or position connecting portion 28 toward first passage 22. This in turn changes the shape of passage 22 of coupling body 20 so that connecting portion 28 and arms 26a, 26b contact and frictionally and clampingly engage proximal portion 16 of implant 12. In addition, outer surface 46 of clamping member 40 is engaged by the edges along groove portions 32b, 33b to fix clamping member 40 in position in second passage 24 and prevent it from pivoting therein.

The arrangement of connector assembly 10 allows engagement of elongate member 13 to implant 12 to maintain a low profile in the medial-lateral direction and a nearly tangential proximity of the implant 12 and elongate member 13. Non-perpendicular orientations between elongate member 13 and proximal portion 16 of implant 12 are possible to accommodate engagement of implant 12 with the spinal column and placement of elongate member 13 along the spinal column in various orientations relative to one another. A clamping action about elongate member 13 with clamping member 40 and locking engagement with coupling body 20 maintains the positioning of clamping member 40 and coupling body 20 relative to one another when coupling body 12 is secured to implant 12. Furthermore, the location of connection portion 28 along proximal portion 16 of implant 12 can be adjusted, and coupling body 20 can be secured to implant 12 at any one of a number of positions along proximal portion 16.

In spinal surgical procedures, elongate member 13 and one or more connector assemblies 10 and other implants discussed herein may be employed unilaterally. Alternatively, a second elongate member 13 and one or more connector assemblies 10 and/or other suitable connection mechanism with other implants can be secured to the other side of the vertebral level or levels to be stabilized. Multiple elongate members 13 and corresponding implant/connector assemblies 10 can be secured along the same side of the spinal column in either uni-lateral or bi-lateral stabilization procedures.

In one technique, the underlying bone forms a portion of a vertebral body of the spinal column. The underlying bone can be a part of the anterior, oblique, antero-lateral, lateral or posterior vertebral elements, including the pedicle, spinous process, transverse processes, lamina or facet, for example. Applications in techniques along any portion or portions of the spinal column are contemplated, including the cervical, thoracic, lumbar and sacral regions. The connector assemblies, implants and elongate members can be positioned along the spinal column in invasive procedures where skin and tissue are dissected and retracted to expose the implant locations, or in minimally invasive procedures where one or more of the connector assemblies, elongate members and/or implants are guided through at least the tissue or access portals adjacent the column to the desired implantation location.

While the invention has been illustrated and described in detail in the drawings and foregoing description, the same is to be considered as illustrative and not restrictive in character. All changes and modifications that come within the spirit of the invention are desired to be protected.

What is claimed is:

1. A system for stabilizing a bony segment, comprising:
   an elongate member positionable along the bony segment;
   an implant including a proximal portion and a distal portion engageable to the bony segment with the proximal portion in a transverse orientation to the elongate member;
   a connector assembly for connecting the elongate member to the implant, said connector assembly comprising:
      a coupling body having a pair of arms extending along a first axis and alongside one another between a free end and an opposite end of each of said pair of arms, a connecting portion extending along a second axis transverse to said first axis, said connecting portion extending transversely between and interconnecting said pair of arms at said opposite ends, said connecting portion defining a first passage receiving said proximal portion of said implant therethrough and said pair of arms defining a second passage receiving said elongate member therethrough in said transverse orientation;
      a clamping member positioned in said second passage and extending at least partially about said elongate member in said second passage; and
      an engaging member engaged to said first arm in a first position, wherein said engaging member is movable toward said clamping member from said first position to a second position in contact with said clamping member to clampingly engage said clamping member to said elongate member while flexing said coupling body about said connecting portion, said flexing transitions said coupling body to a deformed configuration wherein said pair of arms are deformed apart in opposite directions away from one another and wherein said connecting portion is deformed into said first passage such that said first passage changes shape to engage said connecting portion of said coupling body to said proximal portion of said implant.

2. The system of claim 1, wherein said clamping member is pivotal in said second passage when said engaging member is in said first position.

3. The system of claim 2, wherein said first and second arms each include an inner surface facing the other inner surface and defining said second passage, and further comprising at least one groove about said inner surface of at least one of said first and second arms, said groove including a number of edges for biting into an outer surface of said clamping member when said clamping member is clampingly engaged to said elongate member.

4. The system of claim 1, wherein said coupling body includes a gap between said pair of arms, said gap including a first portion extending from said outer ends of said pair of arms to said connecting portion, said gap being in communication with each of said first and second passages.

5. The system of claim 4, wherein said gap includes a second portion along said connecting portion extending transversely to said first portion of said gap and forming reliefs extending along said connecting portion.

6. The system of claim 1, wherein said first arm includes an internally threaded receptacle in communication with said second passage and said engaging member is threadingly engaged to said first arm in said first receptacle.

7. The system of claim 1, wherein said implant is a bone screw including a proximal portion in the form of a post positioned through said first passage and said elongate member is a spinal rod.

8. The system of claim 1, wherein said coupling body is configured to move said first arm along said engaging member and away from said clamping member as said engaging member is moved from said first position to contact said clamping member thereby flexing said coupling body about said connecting portion to clampingly engage said coupling body to said proximal portion of said implant.

9. A system for stabilizing a bony segment, comprising:
   an elongate member positionable along the bony segment;
   an implant including a proximal portion and a distal portion engageable to the bony segment with the proximal portion in a transverse orientation to the elongate member;
   a connector assembly for connecting the elongate member to the implant, said connector assembly comprising:
      a coupling body having a connecting portion extending along a first axis and transversely between and interconnecting a pair of arms, said arms extending from said connecting portion along a second axis transverse to said first axis and extending alongside one another and forming a gap therebetween, said connecting portion defining a first passage receiving said proximal portion of said implant therethrough and said pair of arms defining a second passage receiving said elongate member therethrough in said transverse orientation;
      a clamping member positioned in said second passage and extending at least partially about said elongate member in said second passage; and
      an engaging member engaged to said first arm in a first position, wherein said coupling body is configured to move said first arm along said engaging member and away from said clamping member as said engaging member is moved from said first position to a second position in contact with said clamping member to clampingly engage said clamping member to said elongate member, wherein movement of said first arm bends said coupling body about said connecting portion, said movement of said first arm transitions said coupling body to a deformed configuration wherein said pair of arms are deformed apart in opposite directions away from one another and wherein said connecting portion is deformed into said first passage such that said first passage changes shape to frictionally engage said connecting portion of said coupling body to said proximal portion of said implant in said first passage.

10. The system of claim 9, wherein said clamping member is pivotal in said second passage when said engaging member is in said first position.

11. The system of claim 9, wherein said gap includes a second portion along said connecting portion extending transversely to said first portion of said gap and forming reliefs extending along said connecting portion.

12. The system of claim 9, wherein said first arm includes an internally threaded receptacle in communication with said second passage and said engaging member is threadingly engaged to said first arm in said receptacle.

13. The system of claim 9, wherein said implant is a bone screw and said distal portion is a threaded shaft and said proximal portion is a smooth post.

14. A system for stabilizing a bony segment, comprising:
an elongate member positionable along the bony segment;
an implant including a proximal portion and a distal portion engageable to the bony segment with the proximal portion in a transverse orientation to the elongate member;
a connector assembly for connecting the elongate member to the implant, said connector assembly comprising:
a coupling body having a connecting portion extending between a pair of arms, said arms extending from said connecting portion alongside one another and forming a gap therebetween, said connecting portion defining a first passage receiving said proximal portion of said implant therethrough and said pair of arms defining a second passage receiving said elongate member therethrough in said transverse orientation, wherein a first of said arms includes an internally threaded receptacle in communication with said second passage and an engaging member is threadingly engaged to said first arm in said receptacle;
a clamping member positioned about said elongate member in said second passage; and
said engaging member engaged to said first arm in a first position, wherein said coupling body is configured to move said first arm along said engaging member and away from said clamping member as said engaging member is moved from said first position to contact said clamping member and clampingly engage said clamping member to said elongate member, wherein movement of said first arm bends said coupling body about said connecting portion and frictionally engages said coupling body to said proximal portion of said implant in said first passage, wherein said engaging member includes a distal end surface having a concave curvature and said clamping member includes a concavely curved outer surface engaged by said distal end surface of said engaging member when said engaging member contacts said clamping member.

15. A method for coupling an elongate member to an implant engageable to a spinal column, comprising:
engaging the implant to a vertebra of the spinal column;
positioning an elongate member along the spinal column in a transverse orientation to the implant;
positioning a clamping member about the elongate member;
positioning a proximal portion of the implant in a first passage of a coupling body;
positioning the clamping member in a second passage of the coupling body;
engaging an engaging member to the coupling body; and
contacting the engaging member to the clamping member to clamp the clamping member about the elongate member while simultaneously bending the coupling body with the engaging member to clampingly engage the coupling body to the proximal portion of the implant in the first passage, wherein the coupling body includes a connecting portion and a pair of arms extending from the connecting portion alongside one another, and bending the coupling body includes moving at least one of the arms away from the other about the connecting portion.

16. The method of claim 15, wherein engaging the engaging member includes threading the engaging member into a first arm of the coupling body toward the clamping member in the second passage.

17. The method of claim 16, wherein bending the coupling body includes displacing the first arm along the engaging member and away from the clamping member as the engaging member is threaded into contact with the clamping member.

18. The method of claim 15, further comprising adjusting a position of the coupling body along the proximal portion of the implant before bending the coupling body.

19. The method of claim 15, wherein the clamping member is pivotal in the second passage and contacting the engaging member to the clamping member fixes the clamping member in position in the second passage.

20. The method of claim 15, wherein the bending of the coupling member results in transitioning of the coupling body to a deformed configuration, the transitioning comprising:
moving the pair of arms apart in opposite directions away from one another; and
deforming the connecting portion into the first passage and changing the shape of the first passage to thereby engage the connecting portion of the coupling body to the proximal portion of the implant.

* * * * *

UNITED STATES PATENT AND TRADEMARK OFFICE
CERTIFICATE OF CORRECTION

PATENT NO. : 7,585,299 B2   Page 1 of 1
APPLICATION NO. : 11/356939
DATED : September 8, 2009
INVENTOR(S) : Alan Rezach It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 611 days.

Signed and Sealed this

Fourteenth Day of September, 2010

David J. Kappos
*Director of the United States Patent and Trademark Office*